United States Patent [19]

Wechter et al.

[11] 4,172,889

[45] Oct. 30, 1979

[54] METHOD OF TREATING RHEUMATOID ARTHRITIS

[75] Inventors: William J. Wechter, Kalamazoo; Carter D. Brooks, Texas Township, Kalamazoo County, both of Mich.

[73] Assignee: The Upjohn Company, Kalamazoo, Mich.

[21] Appl. No.: 895,674

[22] Filed: Apr. 12, 1978

Related U.S. Application Data

[62] Division of Ser. No. 671,289, Mar. 29, 1976, Pat. No. 4,118,484.

[51] Int. Cl.$^2$ .................... A61K 31/70; C07H 19/08
[52] U.S. Cl. ........................................ 424/180; 536/23
[58] Field of Search ........................... 424/180; 536/23

[56] References Cited

U.S. PATENT DOCUMENTS

| | | | |
|---|---|---|---|
| 3,894,000 | 7/1975 | Wechter et al. | 536/23 |
| 3,920,630 | 11/1975 | Wechter et al. | 536/23 |

OTHER PUBLICATIONS

Glenn, E. Myles, "Proc. Soc. Exptl. Biol. and Med.", 129, pp. 860–864, 1968.
Gray et al., "Biochemical Pharmacology", vol. 21, pp. 465–475, Pergamon Press, 1972, Great Britain.
Wechter et al., "Jour. of Medicinal Chem.", vol. 18, No. 4, 1975, pp. 339–344.

*Primary Examiner*—Johnnie R. Brown
*Attorney, Agent, or Firm*—William G. Jameson; Sidney B. Williams, Jr.

[57] ABSTRACT

A process of treatment for the management of the condition known as rheumatoid arthritis. The process manages rheumatoid arthritis by controlling the inflammatory process in a rheumatoid joint by the intra-articular administration to said joint of an effective amount for controlling the inflammatory process of certain $N^4$-acyl-ara-cytidines, 5'-O-acyl-ara-cytidines and pharmaceutically acceptable acid addition salts thereof, and pharmaceutically acceptable acid addition salts of 5'-O-acyl-2,2'-anhydro-ara-cytidines.

14 Claims, No Drawings

METHOD OF TREATING RHEUMATOID ARTHRITIS

This is a division of application Ser. No. 671,289, filed Mar. 29, 1976, now U.S. Pat. No. 4,118,484.

BACKGROUND OF THE INVENTION

1. Field of the Invention

The invention concerns a method of treating rheumatoid arthritis in mammals including humans. More specifically, the invention concerns a method of controlling the inflammatory process in a rheumatoid joint of a mammal.

2. Description of the Prior Art

Belgium Pat. No. 773,027 of Mar. 24, 1972, and U.S. Pat. No. 3,920,630 issued Nov. 18, 1975, disclose 2,2'-anhydro-ara-cytidine compounds as useful in the treatment of autoimmune diseases, such as multiple sclerosis and rheumatoid arthritis.

Belgium Pat. No. 773,027 and U.S. Pat. No. 3,920,630 do not disclose which, if any, of the compounds are effective as an intra-articularly administered agent in controlling the inflammatory process in a rheumatoid joint.

2. Description of Additional Art

W. J. Wechter et al., *ara-Cytidine Acylates, Use of Drug Design Predictors in Structure-Activity Relationship Correlation*, J. Med. Chem., 18, 339 (1975) summarize studies on depot ester derivatives of the nucleoside, aracytidine, including 5'-O-benzoyl-ara-cytidine and 5'-O-palmityl-ara-cytidine. The article deals with the development of a depot form of ara-cytidine employing in vitro correlates for the design of a drug for clinical application in cancer and rheumatoid arthritis, the latter to be effective as a locally administered (intra-articular) immunosuppressive agent in rheumatoid joints.

SUMMARY OF THE INVENTION

The invention comprises a method of controlling the inflammatory process in a rheumatoid joint of a mammal which comprises the intra-articular administration to said joint of an effective amount for controlling the inflammatory process of a member selected from the group consisting of a $N^4$-acyl-ara-cytidine, a 5'-O-acyl-ara-cytidine or a pharmaceutically acceptable acid addition salt thereof, and a pharmaceutically acceptable acid addition salt of a 5'-O-acyl-2,2'-anhydro-ara-cytidine; each of said member characterized by having the formula:

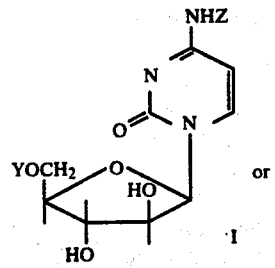

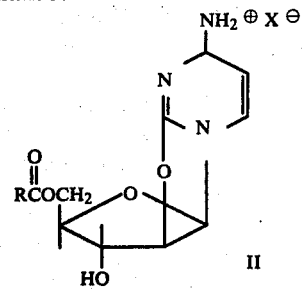

wherein $X^\ominus$ is the conjugate base of a strong acid; R is a radical selected from the group consisting of a straight or branched chain aliphatic radical of from 1 through 20 carbon atoms, an aromatic radical of from 6 through 10 carbon atoms, a monocyclic aliphatic radical of from 4 through 10 carbon atoms, an araliphatic radical of from 7 through 12 carbon atoms; a cage-type hydrocarbon radical containing from 7 through 20 carbon atoms, and including such radicals substituted by halogen, hydroxyl, carboxyl, nitro, alkoxy or mercapto substituent groups, and R when taken together with

is the acyl radical of an aliphatic dicarboxylic acid of from 3 through 8 carbon atoms; Y is hydrogen or an acyl radical of an organic carboxylic acid;

in which R is as defined above; Z is hydrogen or an acyl radical of an organic carboxylic acid,

in which R' is a radical selected from the group consisting of β,β,β-trihaloethoxy, a straight or branched chain aliphatic radical of from 14 through 22 carbon atoms, an aromatic radical of from 6 through 10 carbon atoms, including such radicals substituted by halogen, hydroxyl, carboxyl, nitro or alkoxy substituent groups; and provided that when Y is hydrogen, Z is an acyl radical of an organic carboxylic acid,

as defined above; and further provided that when Z is hydrogen, Y is an acyl radical of an organic carboxylic acid,

as defined above; and being further characterized by having:
  (a) an enzymatic hydrolysis rate in human rheumatoid synovial fluid equal to or greater than the enzymatic hydrolysis rate of 5'-O-1-adamantoylara-cytidine, and (b) an aqueous solubility of less than about 300 μg./ml. for:
(1) the compounds wherein Z is hydrogen, or
(2) the base form of pharmaceutically acceptable acid addition salts of compounds wherein Z is hydrogen, or
(3) the compounds wherein Y is hydrogen, or
(4) the base form of the 5'-O-acyl-2,2'-anhydroara-cytidine compounds.

Certain of the compounds are hygroscopic and readily form hydrates. The hydrated forms, such as for example the hydrate of 5'-O-benzoyl-ara-cytidine, may be employed in the same manner as the non-hydrated form. It is to be understood that reference to such compounds in this specification and claims includes the hydrates thereof.

All of these compounds are known or can be prepared by known methods. See, for example, U.S. Pat. Nos. 3,847,898; 3,920,630; 3,317,512; 3,337,530; 3,300,478; and German Offlengschrift No. 2,426,304 (Jan. 2, 1975).

The term "pharmaceutically acceptable acid addition salt" as used throughout the specification and claims means salts formed with an acid providing an anion which is pharmacologically acceptable to the host body as well as acceptable for pharmaceutical compounding. Illustrative examples of pharmaceutically acceptable acid addition salts are hydrochloride, sulfate, acetate and the like.

The term "strong acid" as used throughout the specification and claims means an acid providing an anion which is pharmacologically acceptable to the host body as well as acceptable for pharmaceutical compounding and which is sufficiently strong enough to react with the amino grouping of the cytosine moiety, thereby forming a pharmaceutically acceptable acid addition salt. Illustrative examples of strong pharmaceutically acceptable acids are hydrochloric, sulfuric, acetic and the like.

Pharmaceutically acceptable acid addition salts of compounds of Formula Ia are converted in vivo to the corresponding 5'-O-acyl-ara-cytidine, i.e., the base form.

Pharmaceutically acceptable acid addition salts of compounds of Formula II are converted in vivo to the corresponding 5'-O-acyl-ara-cytidine (Ia). The in vivo conversion of a pharmaceutically acceptable acid addition salt of a compound of Formula II is illustrated by the schematic formula:

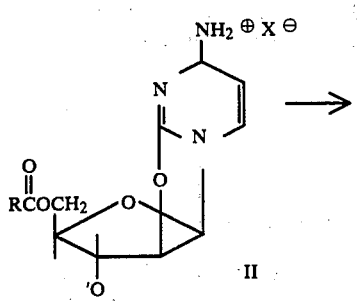

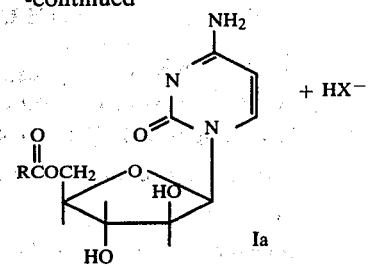

wherein R and X⊖ are as previously defined.

In the above formulae, compounds of the formula Ia are the base form of compounds of Formula II.

The term "enzymatic hydrolysis rate in human rheumatoid synovial fluid equal to or greater than the enzymatic hydrolysis rate of 5'-O-1-adamantoyl-ara-cytidine" as used throughout the specification and claims means an enzymatic hydrolysis rate, to yield ara-cytidine, in human rheumatoid synovial fluid equal to or greater than the enzymatic hydrolysis rate in human rheumatoid synovial fluid of 5'-O-1-adamantoyl-ara-cytidine.

DETAILED DESCRIPTION OF THE INVENTION

This invention provides a method of treating rheumatoid arhtritis in mammals by controlling the inflammatory process in a rheumatoid joint.

More specifically, this invention provides a method of controlling the inflammatory process in a rheumatoid joint of a mammal including humans by the intra-articular administration to said joint of an effective amount for controlling the inflammatory process of a member selected from the group consisting of a N⁴-acyl-ara-cytidine, a 5'-O-acyl-ara-cytidine or a pharmaceutically acceptable acid addition salt thereof, and a pharmaceutically acceptable acid addition salt of a 5'-O-acyl-2,2'-anhydro-ara-cytidine; each of said member characterized by having the formula:

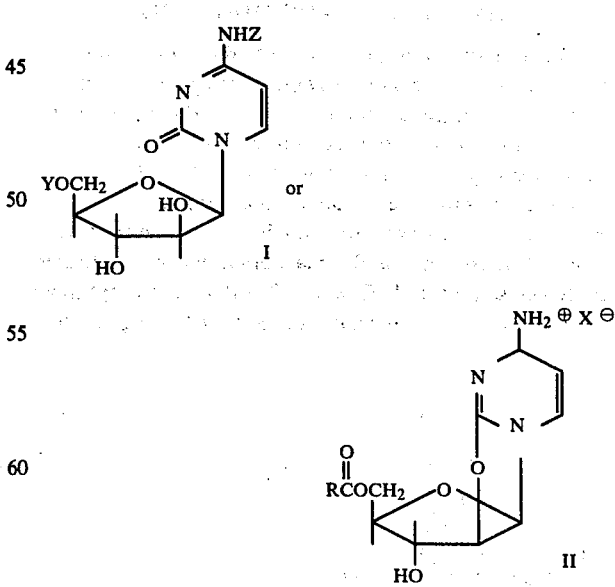

wherein X⊖ is the conjugate base of a strong acid; R is a radical selected from the group consisting of a straight or branched chain aliphatic radical of from 1 through 20 carbon atoms, an aromatic radical of from 6 through 10 carbon atoms, a monocyclic aliphatic radical of from 4 through 10 carbon atoms, an araliphatic radical of from 7 through 12 carbon atoms, a cage-type hydrocarbon radical containing from 7 through 20 carbon atoms, and including such radicals substituted by halogen, hydroxyl, carboxyl, nitro, alkoxy or mercapto substituent groups, and R when taken together with $$\overset{O}{\underset{C}{\|}}$$

is the acyl radical of an aliphatic dicarboxylic acid of from 3 through 8 carbon atoms; Y is hydrogen or an acyl radical of an organic carboxylic acid;

$$\overset{O}{\underset{RC-}{\|}},$$

in which R is as defined above; Z is hydrogen or an acyl radical of an organic carboxylic acid, $$\overset{O}{\underset{R'C-}{\|}},$$

in which R' is a radical selected from the group consisting of β,β,β-trihaloethoxy, a straight or branched chain aliphatic radical of from 14 through 22 carbon atoms, an aromatic radical of from 6 through 10 carbon atoms, including such radicals substituted by halogen, hydroxyl, carboxyl, nitro or alkoxy substituent groups; and provided that when Y is hydrogen, Z is an acyl radical of an organic carboxylic acid, $$\overset{O}{\underset{R'C-}{\|}},$$

as defined above; and further provided that when Z is hydrogen, Y is an acyl radical of an organic carboxylic acid, $$\overset{O}{\underset{RC-}{\|}},$$

as defined above; and being further characterized by having:
(a) an enzymatic hydrolysis rate in human rheumatoid synovial fluid equal to or greater than the enzymatic hydrolysis rate of 5'-O-1-adamantoyl-ara-cytidine, and
(b) an aqueous solubility of less than about 300 μg./ml. for:
(1) the compounds wherein Z is hydrogen, or
(2) the base form of pharmaceutically acceptable acid addition salts of compounds wherein Z is hydrogen, or
(3) the compounds wherein Y is hydrogen, or
(4) the base form of the 5'-O-acyl-2,2'-anhydroaracytidine compounds.

Representative values of R in the foregoing are 1-chloro-2,3-dimethylbutyl, 2,2-dimethylpropyl, 1-mercapto-2,2-dimethylpropyl, phenyl, 2-methylphenyl, 2,5-dimethylphenyl, 2,4,6-trimethylphenyl, 1-naphthyl, 2-naphthyl,

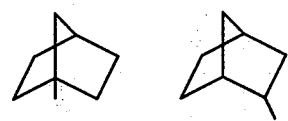
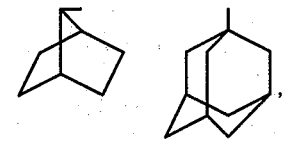
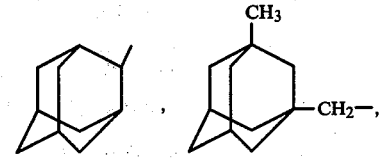
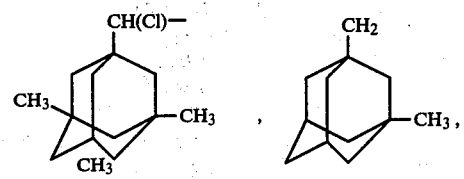
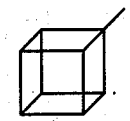

and also groups which, together with the $$\overset{O}{\underset{-C-}{\|}}$$

group make up the acyl group of polycarboxylic acids such as glutamic, glutaric, succinic, fumaric, aconitic, itaconic, levulinic, 3,3-dimethylglutaric and other 3,3-dialkylglutaric acids and other acids as will be exemplified later.

A group of compounds within the scope of Formula I are those wherein Z is hydrogen and Y is the acyl radical of a saturated or unsaturated fatty acid of from 7 through 20 carbon atoms.

Another group of compounds within the scope of Formula I are those wherein Y is hydrogen and Z is the acyl radical of a saturated or unsaturated fatty acid of from 14 through 22 carbon atoms.

One group of compounds of Formula I are those of Formula Ia and pharmaceutically acceptable acid addition salts thereof:

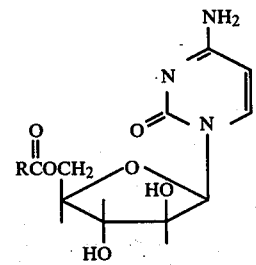

wherein R is as defined above.
Illustrative compounds of Formula Ia are

5'-O-palmityl-ara-cytidine,
5'-O-lauryl-ara-cytidine,
5'-O-oleyl-ara-cytidine,
5'-O-nitrobenzoyl-ara-cytidine,
5'-O-o-toluoyl-ara-cytidine,
5'-O-benzoyl-ara-cytidine,
5'-O-1-fluorenecarbonyl-ara-cytidine,
5'-O-1-naphthoyl-ara-cytidine,
5'-O-1-indenecarbonyl-ara-cytidine,
5'-O-p-anisoyl-ara-cytidine,
5'-O-1-norbornylcarbonyl-ara-cytidine,
5'-O-1-adamantoyl-ara-cytidine,
5'-O-[(α-chloro-3,5,7-trimethyl-1-adamantyl)acetyl]-ara-cytidine,
5'-O-(1-xanthylcarbonyl)-ara-cytidine,
5'-O-4-cinnolinoyl-ara-cytidine, and pharmaceutically acceptable acid addition salts thereof, for example:
5'-O-palmityl-ara-cytidine hydrochloride,
5'-O-lauryl-ara-cytidine hydrochloride,
5'-O-oleyl-ara-cytidine hydrochloride,
5'-O-nitrobenzoyl-ara-cytidine hydrochloride,
5'-O-o-tolueyl-ara-cytidine hydrochloride,
5'-O-benzoyl-ara-cytidine hydrochloride,
5'-O-1-fluorenecarbonyl-ara-cytidine hydrochloride,
5'-O-1-naphthoyl-ara-cytidine hydrochloride,
5'-O-1-indenecarbonyl-ara-cytidine hydrochloride,
5'-O-p-anisoyl-ara-cytidine hydrochloride,
5'-O-1-norbornylcarbonyl-ara-cytidine hydrochloride,
5'-O-1-adamantoyl-ara-cytidine hydrochloride,
5'-O-[(α-chloro-3,5,7-trimethyl-1-adamantyl)acetyl]ara-cytidine hydrochloride,
5'-O-(10-xanthylcarbonyl)-ara-cytidine hydrochloride,
5'-O-4-cinnolinoyl-ara-cytidine hydrochloride.

A group of compounds within the scope of Formula Ia are those wherein R is an aliphatic radical of from 1 through 20 carbon atoms, or a pharmaceutically acceptable acid addition salt thereof.

Another group of compounds within the scope of Formula Ia are those wherein R is an aromatic radical of from 6 through 10 carbon atoms, or a pharmaceutically acceptable acid addition salt thereof.

Another group of compounds of Formula I are those of Formula Ib:

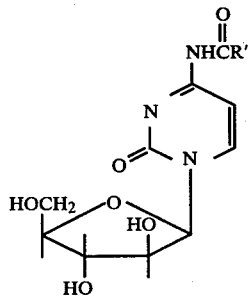

wherein R' is as defined above.

A group of compounds of Formula Ib are those wherein R' is a radical selected from the group consisting of β,β,β-trichloroethoxy, a straight chain aliphatic radical of from 14 through 22 carbon atoms, phenyl, and p-methoxyphenyl.

Illustrative compounds of Formula Ib are
$N^4$-trichloroethoxycarbonyl-ara-cytidine,
$N^4$-benzoyl-ara-cytidine,
$N^4$-p-anisoyl-ara-cytidine,
$N^4$-pentadecanoyl-ara-cytidine,
$N^4$-palmityl-ara-cytidine,
$N^4$-stearyl-ara-cytidine,
$N^4$-oleyl-ara-cytidine,
$N^4$-arachidoyl-ara-cytidine,
$N^4$-arachidonoyl-ara-cytidine,
$N^4$-behenoyl-ara-cytidine,
$N^4$-docosyl-ara-cytidine, Compounds of Formula II are those of the formula:

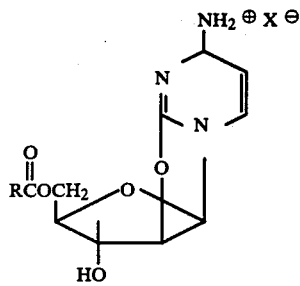

wherein R and $X^\ominus$ is as defined above.

A group of compounds within the scope of Formula II are those wherein R is an aliphatic radical of from 1 through 20 carbon atoms.

Another group of compounds within the scope of Formula II are those wherein R is an aromatic radical of from 6 through 10 carbon atoms.

Illustrative compounds of Formula II are
5'-O-palmityl-2,2'-anhydro-ara-cytidine hydrochloride,
5'-O-lauryl-2,2'-anhydro-ara-cytidine hydrochloride,
5'-O-oleyl-2,2'-anhydro-ara-cytidine hydrochloride,
5'-O-nitrobenzoyl-2,2'-anhydro-ara-cytidine hydrochloride,
5'-O-o-toluoyl-2,2'-anhydro-ara-cytidine hydrochloride,
5'-O-benzoyl-2,2'-anhydro-ara-cytidine hydrochloride,
5'-O-1-fluorenecarbonyl-2,2'-anhydro-ara-cytidine hydrochloride,
5'-O-1-naphthoyl-2,2'-anhydro-ara-cytidine hydrochloride,
5'-O-1-indenecarbonyl-2,2'-anhydro-ara-cytidine hydrochloride,
5'-O-p-anisoyl-2,2'-anhydro-ara-cytidine hydrochloride,
5'-O-1-norbornylcarbonyl-2,2'-anhydro-ara-cytidine hydrochloride,
5'-O-1-adamantoyl-2,2'-anhydro-ara-cytidine hydrochloride,
5'-O-[(α-chloro-3,5,7-trimethyl-1-adamantyl)acetyl]-2,2'-anhydro-ara-cytidine hydrochloride,
5'-O-(10-xanthylcarbonyl)-2,2'-anhydro-ara-cytidine hydrochloride,
5'-O-4-cinnolinoyl-2,2'-anhydro-ara-cytidine hydrochloride,
5'-O-2-indolylcarbonyl-2,2'-anhydro-ara-cytidine hydrochloride, and other pharmaceutically acceptable acid addition salts thereof.

Rheumatoid arthritis is a systemic disease characterized by a progressive inflammatory involvement of the articulations, and by atrophy of muscles and rarefaction of bones. According to the present invention, certain known ara-cytidine and 2,2'-anhydro-ara-cytidine analogs suitably combined with pharmaceutical means which adapt the combination of intra-articular administration are beneficial in controlling the inflammatory process in a rheumatoid joint. Controlling the inflammatory process as referred to in this invention means decreases swelling, pain, heat and stiffness resulting in improved joint function.

Any peripheral rheumatoid joint, including for example, the knee, shoulder, hip, elbow, wrist, ankle, tarsal, and the like, can be injected as well as the temporomandibular, acromioclavicular or sternoclavicular joints. The anatomic structure and depth below the body surface of the spinal joints make local attempts to treat such articulations impractical, however, any rheumatoid peripheral joint can be injected.

The dosage of a 5'-O-acyl-ara-cytidine (Ia) or pharmaceutically acceptable acid addition salt thereof, or a $N^4$-acyl-ara-cytidine (Ib), or a pharmaceutically acceptable acid addition salt of a 5'-O-acyl-2,2'-anhydro-ara-cytidine (II); characterized by having an aqueous solubility as defined hereinbefore and an enzymatic hydrolysis rate in human rheumatoid synovial fluid equal to or greater than the enzymatic hydrolysis rate of 5'-O-1-adamantoyl-ara-cytidine, depends upon the joint to be treated (e.g., the size of the joint), the circumstances of treatment (e.g., severity of disease and adjuvant therapy), the species of mammal to be treated, as well as the subject's age, weight and general physical condition. In general, a dose of from about 10 to about 1,000 mg. in a single dose administered intra-articularly to the joint is effective. More specifically, the dose is from about 10 to about 500 mg. of the compound.

Illustratively, dosage levels in humans of the administered active ingredients can be: knee, about 100 to about 400 mg. per joint injection; shoulder, about 100 to about 600 mg. per joint injection; metacarpal or proximal intraphalangeal, about 10 to about 100 mg. per joint; and elbow, about 100 to about 300 mg. per joint.

The frequency of subsequent injections into a given joint are spaced to the time of recurrence of symptoms in the joint and the avoidance of systemic toxicities such as bone marrow depression, hepatotoxicity, diarrhea and abdominal pain. Bone marrow depression can be evidenced by megaloglastosis, reduction of lymphocyte count or reduction of granulocyte count.

When it is desired to inject numerous joints, a plan of treatment should be arranged so that the number of joints injected at one time does not result in systemic toxicities such as bone marrow depression, hepatotoxicity, diarrhea and abdominal pain.

For intra-articular administration, fluid dose preparations are prepared utilizing the compound and a sterile vehicle, water being preferred. In preparing aqueous suspensions, the compound can be sterilized by exposure to ethylene oxide before suspending in water for injection and filling into a suitable vial or ampul and sealing. Advantageously, adjuvants such as a local anesthetic, preservative and buffering agents can be dissolved in the water for injection and filter-sterilized before suspending the sterilized compound. A surfactant or wetting agent can be included in the composition to facilitate uniform distribution of the compound.

The concentration of the compound (Ia) or the pharmaceutically acceptable acid addition salts thereof or compound (Ib) or compound II is adjusted so that an injection, for example, 0.5 ml., 1.0 ml., and 2.0 ml. provides an effective amount to produce the desired pharmaceutical effect.

The fluid unit dose preparations are packaged, for example, in an ampul or a syringe with a needle. The multiple-dose package, for example, is a vial.

All preparations for intra-articular administration must be sterile, as is known and practiced in the art.

The enzymatic hydrolysis rate of a 5'-O-acyl-ara-cytidine (Ia), pharmaceutically acceptable acid addition salts thereof, or a $N^4$-acyl-ara-cytidine (Ib) or a 5'-O-acyl-2,2'-anhydro-ara-cytidine pharmaceutically acceptable acid addition salt (II) in human rheumatoid synovial fluid can be determined in accordance with the procedure described in Examples 1 and 2.

The determination of the aqueous solubility of a 5'-O-acyl-ara-cytidine (I), a $N^4$-acyl-ara-cytidine (Ib), or the base form of a 5'-O-acyl-2,2'-anhydro-ara-cytidine pharmaceutically acceptable acid addition salt (II) can be dtermined by procedures known in the art, see, e.g., Gray, et al., Biochem. Pharmacology 21, 465 (1972).

The following preparations and method describe the manner and process of making and using this invention and are to be construed as exemplary embodiments of the inventive concept and not as limitations thereof.

EXAMPLE 1

Enzymatic hydrolysis rate of 5'-O-1-adamantoyl-ara-cytidine

Human rheumatoid synovial fluid samples (1 ml.) are preincubated (37° C., 30 min.) with 20 μg. of tetrahydrouridine [THU, 1-(β-D-ribofuranosyl)-4-hydroxy-3,4,5,6-tetrahydropyrimidin-2-(1H)one]. THU is employed to inhibit deamination of the hydrolysis product ara-C to ara-U [Hanze, A. R., J. Amer. Chem. Soc., 89, 6720 (1967)].

A zero-time, 20 μl. of 5'-O-1-adamantoyl-ara-cytidine in dimethylsulfoxide (2 mg./ml.) is added to the synovial fluid sample. At designated time intervals (0, 10, 30 and 240 minutes), aliquots (0.15 ml.) are removed and added to 0.3 ml. absolute ethanol to precipitate proteins. The protein precipitate is removed by centrifugation, and the supernatant assayed using the *Streptococcus faecalis* assay for ara-C [Hanka, L. J., et al., Cancer Chemother. Rep., 54, 393 (1970)].

Standard ara-C samples are prepared in supernatants obtained by adding a double volume of absolute ethanol to a volume of the synovial fluid. Ara-C is added to the supernatant in concentrations ranging from 0.0625 to 8 μg./ml. A control sample containing no drug is also assayed. After appropriate incubation, diameters of zones of inhibition are measured. Linear regression analysis of log ara-C concentrations vs. zone diameter provide the standard curve for determination of ara-C concentration in the samples. Appropriate controls are also run in $NH_4Cl$ buffer (pH 7.45) to determine rates of non-enzymatic hydrolysis and all rates corrected for this factor.

The hydrolysis rate is determined from plots of ara-C concentration vs. time. Semilogarithmic plots of ester concentration vs. time show hydrolysis to follow first-order kinetics.

For 5'-O-1-adamantoyl-ara-cytidine, the enzymatic hydrolysis rate is 1.5 min.$^{-1}$.

EXAMPLE 2

Enzymatic hydrolysis rate of 5'-O-benzoyl-ara-cytidine, monohydrate

Human rheumatoid synovial fluid samples (1 ml.) are preincubated (37° C., 30 min.) with 20 μg. of tetrahydrouridine [THU, 1-(β-D-ribofuranosyl)-4-hydroxy-3,4,5,6-tetrahydropyrimidin-2-(1H)one]. THU is employed to inhibit deamination of the hydrolysis product ara-C to ara-U [Hanze, A. R., J. Amer. Chem. Soc., 89, 6720 (1967)].

At zero-time, 20 μl. of 5'-O-benzoyl-ara-cytidine, monohydrate in dimethylsulfoxide (2 mg./ml.) is added to the synovial fluid sample. At designated time intervals (0, 10, 30 and 240 minutes) aliquots (0.15 ml.) are removed and added to 0.3 ml. absolute ethanol to precipitate proteins. The protein precipitate is removed by centrifugation, and the supernatant assayed using the *Streptococcus faecalis* assay for ara-C [Hanka, L. J., et al. Cancer Chemother. Rep., 54, 393 (1970)].

Standard ara-C samples are prepared by supernatants obtained by adding a double volume of absolute ethanol to a volume of the synovial fluid. Ara-C is added to the supernatant in concentrations ranging from 0.0625 to 8 μg./ml. A control sample consisting no drug is also assayed. After appropriate incubation, diameters of zones of inhibition are measured. Linear regression analysis of log ara-C concentrations vs. zone diameter provide the standard curve for determination of ara-C concentration in the samples. Appropriate controls are also run in NH$_4$Cl buffer (pH 7.45) to determine rates of nonenzymatic hydrolysis and all rates corrected for this factor.

The hydrolysis rate is determined from plots of ara-C concentration vs. time. Semilogarithmic plots of ester concentration vs. time show hydrolysis to follow first-order kinetics.

For 5'-O-benzoyl-ara-cytidine, monohydrate the enzymatic hydrolysis rate is 6.6 min.$^{-1}$.

EXAMPLE 3

Sterile Aqueous Suspension (I)

Part I

A sterile vehicle is prepared from the following types and amounts of ingredients:

| | |
|---|---|
| Methylparaben U.S.P. | 665.300 gm. |
| Propylparaben U.S.P. | 73.920 gm. |
| Sodium chloride - Fine Crystals Reagent | 3168.000 gm. |
| Polyethylene Glycol 4000 U.S.P. | 10560.000 gm. |
| Polysorbate 80 U.S.P. Food Grade | 704.000 gm. |
| Water for Injection U.S.P., q.s.a.d. | 352.000 liters |

DIRECTIONS

Heat approximately 290 liters of water for injection to 65°–75° C. Dissolve the parabens in the heated water for injection. Cool to 25° C. and then dissolve the sodium chloride and polyethylene glycol. Add the Polysorbate 80 and adjust the volume to 352 liters with water for injection. Adjust the pH to 6.0 to 7.0 using, if necessary, 10% aqueous solution sodium hydroxide or 10% aqueous solution hydrochloric acid. Sterilize by filtering through a sterile membrane filter assembly fitted with a sterilizing filter.

Part II

100 Milliliters of suspension is prepared to contain 100 mg. per ml. of the monohydrate of 5'-O-benzoyl-ara-cytidine.

| | |
|---|---|
| 5'-O-benzoyl-ara-cytidine, monohydrate sterile micronized | 10 grams |
| Part I, q.s.a.d. | 100 ml. |

DIRECTIONS

In a sterile container add 75 ml. of the sterile vehicle (Part I) and commence stirring. Slowly add the sterilized micronized 5'-O-benzoyl-ara-cytidine, monohydrate. After all the compound is wetted and mixed, q.s. to volume. Continue stirring for 60 minutes. Using aseptic technique, pass the suspension through a sterile homogenizer (hand type) into a sterile receiver. Aseptically fill the suspension into sterile vials and seal the vials.

The aqueous suspension so prepared is useful for controlling the inflammatory process in a rheumatoid wrist joint of a human by the intra-articular administration to said joint of 1.0 milliliters of said composition.

Using the procedure above, sterile aqueous suspensions are similarly prepared containing 5'-O-benzoyl-ara-cytidine monohydrate, in 25, 50 and 150 mg. per ml. amounts by substituting 2.5, 5.0 and 15 grams of 5'-O-benzoyl-ara-cytidine, monohydrate for the 10 grams used above.

An aqueous suspension prepared containing 150 mg. per ml. of 5'-O-benzoyl-ara-cytidine monohydrate can be used for controlling the inflammatory process in a rheumatoid knee joint of a human by the intra-articular administration to said joint of 2.0 milliliters of said composition.

EXAMPLE 4

Sterile Aqueous Suspension (II)

Part I

A sterile vehicle is prepared from the following types and amounts of ingredients:

| | |
|---|---|
| $^{(a)}$Sodium carboxymethylcellulose Low viscosity | 10.363 gms. |
| Sodium chloride fine crystals Reagent | 18.000 gms. |
| Polysorbate 80 U.S.P. Food Grade | 6.000 gms. |
| Benzyl Alcohol NF | 19.800 gms. |
| Water for Injection, U.S.P. q.s.a.d. | 2.000 liters |
| $^{(a)}$Correct to anhydrous base | |

DIRECTIONS

Blend the sodium chloride and sodium carboxymethylcellulose and then slowly add the mixture to 1.92 liters of water for injection. Continue mixing for 15 minutes. Dissolve the polysorbate 80 in the benzyl alcohol and add to the suspension. Adjust the volume of 2.0 liters with water for injection. Heat the stirred suspension to 90° C. and maintain that temperature for 15 minutes. Cool and if necessary, adjust the pH to 6.2–6.35 using 10% aqueous solution sodium hydroxide or 10% aqueous solution hydrochloric acid. Place suspension in a suitable container and sterilize at 121° C. for 60 minutes. Stir the suspension while cooling to room temperature. Pass through sterile 120 mesh screen into sterile container.

Part II

100 Milliliters of suspension is prepared to contain 100 mg. per ml. of the monohydrate of 5'-O-benzoyl-ara-cytidine.

| 5'-O-benzoyl-ara-cytidine, monohydrate sterile micronized | 10 grams |
|---|---|
| Part I, q.s.a.d. | 100 ml. |

DIRECTIONS

In a sterile container add 75 ml. of the sterile vehicle (Part I) and commence stirring. Slowly add the sterilized micronized 5'-O-benzoyl-ara-cytidine, monohydrate. After all the compound is wetted and mixed, q.s. to volume. Continue stirring for 60 minutes. Using aseptic technique, pass the suspension through a sterile homogenizer (hand type) into a sterile receiver. Aseptically fill the suspension into sterile vials and seal the vials.

The aqueous suspension so prepared is useful for controlling the inflammatory process in a rheumatoid proximal intraphalangeal joint of a human by the intra-articular administration to said joint of 0.1 milliliters of said composition.

The aqueous suspension so prepared is also useful for controlling the inflammatory process in a rheumatoid knee joint of a human by the intra-articular administration to said joint of 1.0 milliliters of said composition.

Using the procedure above, sterile aqueous suspensions are similarly prepared containing 5'-O-benzoyl-ara-cytidine, monohydrate in 25, 50 and 150 mg. per ml. amounts by substituting 2.5, 5.0 and 15 grams of 5'-O-benzoyl-ara-cytidine, monohydrate for the 10 grams used above.

An aqueous suspension prepared containing 150 mg. per ml. of 5'-O-benzoyl-ara-cytidine monohydrate can be used for controlling the inflammatory process in a rheumatoid elbow joint of a human by the intra-articular administration to said joint of 1.0 milliliters of said composition.

EXAMPLE 5

Following the procedure of Examples 3 and 4, sterile aqueous suspensions are prepared substituting equimolar amounts of 5'-O-palmityl-ara-cytidine;
5'-O-lauryl-ara-cytidine;
5'-O-1-adamantoyl-ara-cytidine; and
5'-O-p-anisoyl-ara-cytidine for 5'-O-benzoyl-ara-cytidine, monohydrate of Examples 3 and 4 to provide similar therapeutic properties.

EXAMPLE 6

Following the procedure of Examples 3 and 4, sterile aqueous suspensions are prepared substituting equimolar amounts of $N^4$-trichloroethoxycarbonyl-ara-cytidine,
$N^4$-benzoyl-ara-cytidine,
$N^4$-p-anisoyl-ara-cytidine,
$N^4$-pentadecanoyl-ara-cytidine,
$N^4$-palmityl-ara-cytidine,
$N^4$-stearyl-ara-cytidine,
$N^4$-oleyl-ara-cytidine,
$N^4$-arachidoyl-ara-cytidine,
$N^4$-arachidonoyl-ara-cytidine,
$N^4$-behenoyl-ara-cytidine, and
$N^4$-docosyl-ara-cytidine, for 5'-O-benzoyl-ara-cytidine, monohydrate of Examples 3 and 4 to provide similar therapeutic properties.

EXAMPLE 7

Sterile Aqueous Suspension (III)

Part I

A sterile vehicle is prepared from the following types and amounts of ingredients:

| Methylparaben U.S.P. | 665.300 gm. |
|---|---|
| Propylparaben U.S.P. | 73.920 gm. |
| Sodium Chloride - Fine Crystals Reagent | 3168.000 gm. |
| Polyethylene Glycol 4000 U.S.P. | 10560.000 gm. |
| Polysorbate 80 U.S.P. Food Grade | 704.000 gm. |
| Water for Injection U.S.P., q.s.a.d. | 352.000 Liters |

DIRECTIONS

Heat approximately 290 liters of water for injection to 65°–75° C. Dissolve the parabens in the heated water for injection. Cool to 25° C. and then dissolve the sodium chloride and polyethylene glycol. Add the Polysorbate 80 and adjust the volume to 352 liters with water for injection. Sterilize by filtering through a sterile membrane filter assembly fitted with a sterilizing filter.

Part II

100 Milliliters of suspension is prepared to contain 100 mg. per ml. of the monohydrate of 5'-O-benzoyl-ara-cytidine.

| 5'-O-benzoyl-ara-cytidine, monohydrate sterile micronized | 10 grams |
|---|---|
| Part I. q.s.a.d. | 100 ml. |

DIRECTIONS

In a sterile container add 75 ml. of the sterile vehicle (Part I) and commence stirring. Slowly add the sterilized micronized 5'-O-benzoyl-ara-cytidine, monohydrate. After all the compound is wetted and mixed, q.s. to volume. Continue stirring for 60 minutes. Using aseptic technique, pass the suspension through a sterile homogenizer (hand type) into a sterile receiver. Aseptically fill the suspension into sterile vials and seal the vials.

The aqueous suspension so prepared is useful for controlling the inflammatory process in a rheumatoid wrist joint of a human by the intra-articular administration to said joint of 1.0 milliliters of said composition.

Using the procedure above, sterile aqueous suspensions are similarly prepared containing 5'-O-benzoyl-ara-cytidine, monohydrate, in 25, 50 and 150 mg. per ml. amounts by substituting 2.5, 5.0 and 15 grams of 5'-O-benzoyl-ara-cytidine, monohydrate for the 10 grams used above.

An aqueous suspension prepared containing 150 mg. per ml. of 5'-O-benzoyl-ara-cytidine hydrate can be used for controlling the inflammatory process in a rheumatoid knee joint of a human by the intra-articular administration to said joint of 2.0 milliliters of said compositon.

EXAMPLE 8

Following the procedure of Example 7 sterile aqueous suspensions are prepared substituting equimolar amounts of 5'-O-benzoyl-ara-cytidine or the pharmaceutically acceptable acid addition salts of 5'-O-benzoyl-ara-cytidine for the monohydrate of the example.

EXAMPLE 9

Following the procedure of Example 7 sterile aqueous suspensions are prepared substituting equimolar amounts of
  5'-O-palmityl-ara-cytidine:
  5'-O-lauryl-ara-cytidine;
  5'-O-1-adamantoyl-ara-cytidine;
  5'-O-p-anisoyl-ara-cytidine; or the pharmaceutically acceptable acid addition salts of each of the foregoing compounds for 5'-O-benzoyl-ara-cytidine, monohydrate of Example 7 to provide similar therapeutic properties.

EXAMPLE 10

Following the procedure of Example 7, sterile aqueous suspensions are prepared substituting equimolar amounts of the pharmaceutically acceptable acid salts of
  5'-O-benzoyl-2,2'-anhydro-ara-cytidine;
  5'-O-palmityl-2,2'-anhydro-ara-cytidine;
  5'-O-lauryl-2,2'-anhydro-ara-cytidine;
  5'-O-1-adamantoyl-2,2'-anhydro-ara-cytidine; and
  5'-O-p-anisoyl-2,2'-anhydro-ara-cytidine for 5'-O-benzoyl-ara-cytidine, monohydrate of Example 7 to provide similar therapeutic properties.

EXAMPLE 11

Following the procedure of Example 7 sterile aqueous suspensions are prepared substituting equimolar amounts of a 5'-O-acyl-ara-cytidine, characterized by having the formula:

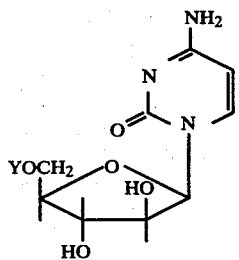

wherein Y is the acyl radical of a saturated or unsaturated fatty acid of from 7 through 20 carbon atoms; and being further characterized by having:
  (a) an enzymatic hydrolysis rate in human rheumatoid synovial fluid equal to or greater than the enzymatic hydrolysis rate of 5'-O-1-adamantoyl-ara-cytidine, and
  (b) an aqueous solubility of less than about 300 μg./ml.; or a pharmaceutically acceptable acid addition salt thereof; for 5'-O-benzoyl-ara-cytidine, monohydrate of Example 7 to provide similar therapeutic properties.

EXAMPLE 12

Following the procedure of Example 7 sterile aqueous suspensions are prepared substituting equimolar amounts of a 5'-O-acyl-ara-cytidine, characterized by having the formula:

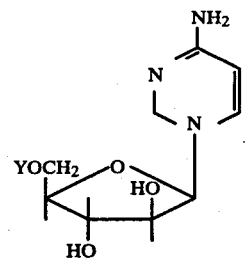

wherein Y is an acyl radical of an organic carboxylic acid,

in which R is an aromatic radical of from 6 through 10 carbon atoms, including said radical substituted by halogen, hydroxyl carboxyl, nitro, alkoxy or mercapto substituent groups; and being further characterized by having:
  (a) an enzymatic hydrolysis rate in human rheumatoid synovial fluid equal to or greater than the enzymatic hydrolysis rate of 5'-O-1-adamantoyl-ara-cytidine, and
  (b) an aqueous solubility of less than about 300 μg./ml.; or a pharmaceutically acceptable acid addition salt thereof; for 5'-O-benzoyl-ara-cytidine, monohydrate of Example 7 to provide similar therapeutic properties.

EXAMPLE 13

Following the procedure of Example 7 sterile aqueous suspensions are prepared substituting equimolar amounts of a member selected from the group consisting of a $N^4$-acyl-ara-cytidine, a 5'-O-acyl-ara-cytidine or a pharmaceutically acceptable acid addition salt thereof, and a pharmaceutically acceptable acid addition salt of a 5'-O-acyl-2,2'-anhydro-ara-cytidine; each of said member characterized by having the formula:

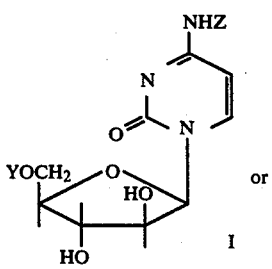

-continued

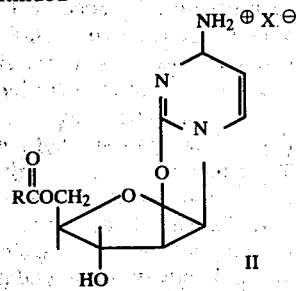

wherein $X^\ominus$ is the conjugate base of a strong acid; R is a radical selected from the group consisting of a straight or branched chain aliphatic radical of from 1 through 20 carbon atoms, an aromatic radical of from 6 through 10 carbon atoms, a monocyclic aliphatic radical of from 4 through 10 carbon atoms, an araliphatic radical of from 7 through 12 carbon atoms, a cage-type hydrocarbon radical containing from 7 through 20 carbon atoms, and including such radicals substituted by halogen, hydroxyl, carboxyl, nitro, alkoxy or mercapto substituent groups, and R when taken together with

is the acyl radical of an aliphatic dicarboxylic acid of from 3 through 8 carbon atoms; Y is hydrogen or an acyl radical of an organic carboxylic acid,

in which R is as defined above; Z is hydrogen or an acyl radical of an organic carboxylic acid,

in which R' is a radical selected from the group consisting of $\beta,\beta,\beta$-trihaloethoxy, a straight or branched chain aliphatic radical of from 14 through 22 carbon atoms, an aromatic radical of from 6 through 10 carbon atoms, including such radicals substituted by halogen, hydroxyl, carboxyl, nitro or alkoxy substituent groups; and provided that when Y is hydrogen, Z is an acyl radical of an organic carboxylic acid,

as defined above; and further provided that when Z is hydrogen, Y is an acyl radical of an organic carboxylic acid,

as defined above; and being further characterized by having:
(a) an enzymatic hydrolysis rate in human rheumatoid synovial fluid equal to or greater than the enzymatic hydrolysis rate of 5'-O-1-adamantoyl-ara-cytidine, and
(b) an aqueous solubility of less than about 300 μg./ml. for:
(1) the compounds wherein Z is hydrogen, or
(2) the base form of pharmaceutically acceptable acid addition salts of compounds wherein Z is hydrogen, or
(3) the compounds wherein Y is hydrogen, or
(4) the base form of the 5'-O-acyl-2,2'-anhydro-ara-cytidine compounds:
for 5'-O-benzoyl-ara-cytidine, monohydrate of Example 7 to provide similar therapeutic properties.

We claim:
1. A method of controlling the inflammatory process in a rheumatoid joint of a mammal which comprises the intra-articular administration to said joint of an effective amount for controlling the inflammatory process of a pharmaceutically acceptable acid addition salt of a 5'-O-acyl-2,2'-anhydro-ara-cytidine, characterized by having the formula:

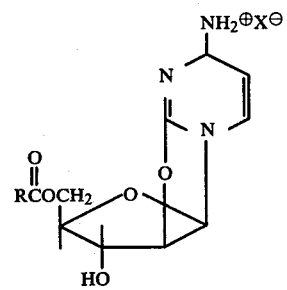

wherein $X^\ominus$ is the congugate base of a strong acid and R is a radical selected from the group consisting of a straight or branched chain aliphatic radical of from 1 through 20 carbon atoms, an aromatic radical of from 6 through 10 carbon atoms, a monocyclic aliphatic radical of from 4 through 10 carbon atoms, an araliphatic radical of from 7 through 12 carbon atoms, a cage-type hydrocarbon radical containing from 7 through 20 carbon atoms, and including such radicals substituted by halogen, hydroxyl, carboxyl, nitro, alkoxy or mercapto substituent groups, and R when taken together with

is the acyl radical of an aliphatic dicarboxylic acid of from 3 through 8 carbon atoms and being further characterized by having:
(a) an enzymatic hydrolysis rate in human rheumatoid synovial fluid equal to or greater than the enzymatic hydrolysis rate of 5'-O-1-adamantoyl-ara-cytidine, and
(b) an aqueous solubility of less than about 300 μg./ml. for the base form of the 5'-O-acyl-2,2'-anhydro-ara-cytidine.

2. The method according to claim 1, wherein R is an aliphatic radical of from 1 through 20 carbon atoms.

3. The method according to claim 1, wherein R is an aromatic radical of from 6 through 10 carbon atoms.

4. The method according to claim 1, wherein the mammal is a human.

5. The method according to claim 4 wherein said pharmaceutically acceptable acid addition salt of 5'-O- acyl-2,2'-anhydro-ara-cytidine is a pharmaceutically acceptable acid addition salt of 5'-O-benzoyl-2,2'-anhydro-ara-cytidine.

6. The method according to claim 4 wherein said pharmaceutically acceptable acid addition salt of 5'-O-acyl-2,2'-anhydro-ara-cytidine is 5'-O-benzoyl-2,2'-anhydro-ara-cytidine hydrochloride.

7. The method according to claim 4 wherein said pharmaceutically acceptable acid addition salt of 5'-O-acyl-2,2'-anhydro-ara-cytidine is a pharmaceutically acceptable acid addition salt of 5'-O-palmityl-2,2'-anhydro-ara-cytidine.

8. The method according to claim 4 wherein said pharmaceutically acceptable acid addition salt of 5'-O-acyl-2,2'-anhydro-ara-cytidine is 5'-O-palmityl-2,2'-anhydro-ara-cytidine hydrochloride.

9. The method according to claim 4 wherein said pharmaceutically acceptable acid addition salt of 5'-O-acyl-2,2'-anhydro-ara-cytidine is a pharmaceutically acceptable acid addition salt of 5'-O-lauryl-2,2'-anhydro-ara-cytidine.

10. The method according to claim 4 wherein said pharmaceutically acceptable acid addition salt of 5'-O-acyl-2,2'-anhydro-ara-cytidine is 5'-O-lauryl-2,2'-anhydro-ara-cytidine hydrochloride.

11. The method according to claim 4 wherein said pharmaceutically acceptable acid addition salt of 5'-O-acyl-2,2'-anhydro-ara-cytidine is a pharmaceutically acceptable acid addition salt of 5'-O-1-adamantoyl-2,2'-anhydro-ara-cytidine.

12. The method according to claim 4 wherein said pharmaceutically acceptable acid addition salt of 5'-O-acyl-2,2'-anhydro-ara-cytidine is 5'-O-1-adamantoyl-2,2'-anhydro-ara-cytidine hydrochloride.

13. The method according to claim 4 wherein said pharmaceutically acceptable acid addition salt of 5'-O-acyl-2,2'-anhydro-ara-cytidine is a pharmaceutically acceptable acid addition salt of 5'-O-p-anisoyl-2,2'-anhydro-ara-cytidine.

14. The method according to claim 4 wherein said pharmaceutically acceptable acid addition salt of 5'-O-acyl-2,2'-anhydro-ara-cytidine is 5'-O-p-anisoyl-2,2'-anhydro-ara-cytidine hydrochloride.

* * * * *

UNITED STATES PATENT AND TRADEMARK OFFICE
CERTIFICATE OF CORRECTION

PATENT NO. : 4,172,889

DATED : October 30, 1979

INVENTOR(S) : William J. Wechter and Carter D. Brooks

It is certified that error appears in the above—identified patent and that said Letters Patent is hereby corrected as shown below:

Column 3, line 17: "form." should read -- forms. --.
Column 3, line 68(of formula II): "'O" should read -- HO --.
Column 7, line 23: "tolueyl" should read -- toluoyl --.

Signed and Sealed this

Twenty-eighth Day of July 1981

[SEAL]

Attest:

Attesting Officer

GERALD J. MOSSINGHOFF

Commissioner of Patents and Trademarks